United States Patent [19]

Putter

[11] 4,144,352
[45] Mar. 13, 1979

[54] MILBEMYCIN COMPOUNDS AS ANTHELMINTIC AGENTS

[75] Inventor: Irving Putter, Martinsville, N.J.

[73] Assignee: Merck & Co., Inc., Rahway, N.J.

[21] Appl. No.: 861,808

[22] Filed: Dec. 19, 1977

[51] Int. Cl.$^2$ ......................................... A61K 31/365
[52] U.S. Cl. .................................................... 424/279
[58] Field of Search ........................................ 424/279

[56] References Cited

U.S. PATENT DOCUMENTS 3,950,360  4/1976  Aoki et al. ............................ 424/279

OTHER PUBLICATIONS

Tetrahedron Letters, vol. 10 (1975), pp. 711–714.
J. of Antibiotics, vol. 29, No. 6, Jun. 1976, pp. 76–14 to 76–16 & 76–35 to 76–42.
Derwent Abstracts, 78836Y/44 (1977).

Primary Examiner—Sam Rosen
Attorney, Agent, or Firm—David L. Rose; Harry E. Westlake

[57] ABSTRACT

The milbemycins are a known series of macrolides, which are disclosed as having insecticidal activity. These compounds have been discovered to have substantial anthelmintic activity. Compositions containing the milbemycin compounds as the active ingredient thereof are also disclosed.

6 Claims, No Drawings

MILBEMYCIN COMPOUNDS AS ANTHELMINTIC AGENTS

BACKGROUND OF THE INVENTION

The milbemycins are a series of thirteen macrolide antibiotics isolated from the fermentation broth of a strain of Streptomyces identified as the B-41-146 strain. Nine of the milbemycin compounds and their preparation are disclosed in U.S. Pat. No. 3,950,360 issued Apr. 13, 1976 to Aoki et al. A complete disclosure of all thirteen of the milbemycin antibiotics is found in the Journal of Antibiotics 29 (6) June 1976 pages 76–35 to 76–42 and pages 76–14 to 76–16. The compounds are disclosed as having insecticidal and acaracidal activity.

SUMMARY OF THE INVENTION

The milbemycins are a series of thirteen compounds which have been disclosed as having insecticidal and acaracidal activity. These compounds have been discovered to be very potent anthelmintic agents. Thus, it is an object of this invention to describe the use of milbemycin compounds as anthelmintic agents. It is a further object of this invention to describe compositions containing one or more of the milbemycin compounds as the active component thereof for use in treating helminthiasis. Further objects will be apparent from reading the following description.

DESCRIPTION OF THE INVENTION

The milbemycins are a series of macrolides which are isolated from the B-41-146 strain of the genus Streptomyces. The milbemycin compounds as originally disclosed in U.S. Pat. No. 3,950,360 consisted of a series of nine compounds, seven of which had had their structures determined. The compounds were named as B-41 antibiotics and given the designation $A_1, A_2, A_3, A_4, B_1, B_2, B_3C_1$ and $C_2$. Since the filing of the original patent application, an additional four compounds have been isolated from the fermentation broth and the structure of all thirteen compounds has been determined. In addition, the nomenclature has been changed from B-41 to milbemycin and the individual designations changed to $\alpha 1$ to $\alpha 10$ and $\beta 1$ to $\beta 3$ recognizing that there are two basic structural differences among the compounds.

The structures of the individual milbemycin compounds and the relationship between the old and new nomenclature is found in the following table:

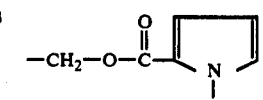

| Milbemycin | $R_1$ | $R_2$ | $R_3$ | $R_4$ | $R_5$ | B-41 |
|---|---|---|---|---|---|---|
| $\alpha_1$ | H | H | $CH_3$ | $CH_3$ | —OH | A3 |
| $\alpha_2$ | H | H | $CH_3$ | $CH_3$ | —$OCH_3$ | B2 |
| $\alpha_3$ | H | H | $C_2H_5$ | $CH_3$ | —OH | A4 |
| $\alpha_4$ | H | H | $C_2H_5$ | $CH_3$ | —$OCH_3$ | B3 |
| $\alpha_5$ | —OH | —OC(O)—CH($CH_3$)—$C_4H_9$ | $CH_3$ | $CH_3$ | —OH | A2 |
| $\alpha_6$ | —OH | —OC(O)—CH($CH_3$)—$C_4H_9$ | $CH_3$ | $CH_3$ | —$OCH_3$ | B1 |
| $\alpha_7$ | —OH | —OC(O)—CH($CH_3$)—$C_4H_9$ | $C_2H_5$ | $CH_3$ | —OH | |
| $\alpha_8$ | —OH | —OC(O)—CH($CH_3$)—$C_4H_9$ | $C_2H_5$ | $CH_3$ | —$OCH_3$ | |
| $\alpha_9$ | H | H | $CH_3$ | —$CH_2$—O—C(O)-pyrrole-NH | —OH | C1 |
| $\alpha_{10}$ | H | H | $C_2H_5$ | —$CH_2$OC(O)-pyrrole-NH | —OH | C2 |

-continued

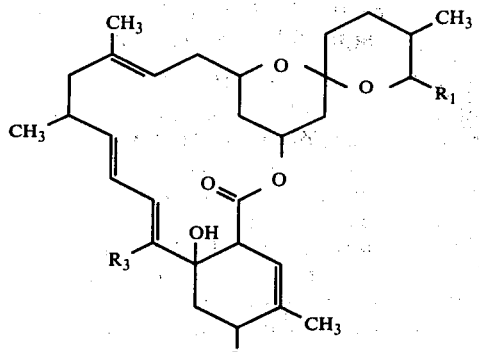

| Milbemycin | $R_1$ | $R_2$ | $R_3$ | B-41 |
|---|---|---|---|---|
| $\beta_1$ | $CH_3$ | $-OCH_3$ | $-CH_2OH$ | $A_1$ |
| $\beta_2$ | $C_2H_5$ | $-OCH_3$ | $-CH_2OH$ | |
| $\beta_3$ | $CH_3$ | $-OH$ | $-CH_3$ | |

The milbemycin compounds are isolated from the fermentation broth by extraction of the mycellia or concentrated filtrate with acetone. The acetone layer is extracted with hexane and concentrated to give a viscous oil. The oil is repeatedly chromatographed on columns of silica gel and alumina, and the columns eluted gradiently with various organic solvent mixtures. Additional chromatographic techniques such as thin layer chromatography and preparative layer chromatography are employed to isolate the individual milbemycin compounds.

The milbemycin compounds of this invention have been found to possess significant parasiticidal activity as anthelmintics in human and animal health.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastro-intestinal tract are the filiarial worms such as Wuchereria, Brugia, Onchocerca and Loa, Dracunculus and extra intestinal stages of the intestinal worms Strongyloides and Trichinella.

These compounds may be administered orally in a unit dosage form such as a capsule, bolus or tablet, or as a liquid drench where used as an anthelmintic in mammals. The drench is normally a solution, suspension or dispersion of the active ingredient usually in water or a suitable non-toxic solvent together with a suspending agent such as bentonite and a wetting agent or like excipient. Generally, the drenches also contain an antifoaming agent. Drench formulations generally contain from about 0.01 to 0.50% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the milbemycin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the anthelmintic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the anthelmintic milbemycin compounds may be administered to animals parenterally, for example, by intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as solketal, glycerol-formal and aqueous parenteral formulations are also used. The active milbemycin compound or compounds are dissolved or suspended in the parenteral formulation for administration; such formulations generally contain from 0.05 to 50% by weight of the active compound.

Milbemycin compounds may also be administered topically by admixture in a suitable vehicle such as dimethylsulfoxide or a hydrocarbon solvent. This preparation is then applied directly to the external surface of the animal by techniques such as spraying or direct pouring.

The optimum amount of active compound to be employed for best results will, of course, depend upon the particular compound employed, the species of animal to be treated and the type and severity of helminthic infection or infestation. Generally, good results are obtained by the oral administration of one or more of the milbemycin compounds at a rate of from about 0.01 to 100.0 mg. per kg. of animal body weight, such total dose being given at one time or in divided doses over a relatively short period of time such as 1-5 days. With the preferred compounds of the invention, excellent control of such parasites is obtained in animals by administering from about 0.5 to 50.0 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the anthelmintic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.5 to 20.0% by weight of the active compound are particularly suitable as feed premixes. Feed supplements, which are fed directly to the animal, contain from about 0.002 to 0.30% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular milbemycin compound or combination of milbemycin compounds employed, the compounds of this invention are usually fed at concentrations of between 0.0001 to 0.02% in the feed in order to achieve the desired antiparasitic result.

In using the compounds of this invention, the individual milbemycin components may be isolated and purified and used in that form. Alternatively, mixtures of two or more of the individual milbemycin components may be used. It is not necessary to completely separate the various milbemycin compounds obtained from the purification of the fermentation broth. Generally, there is obtained a mixture containing two or more of the milbemycin compounds, but having other unrelated compounds excluded therefrom, and such mixture may be used for the prevention and treatment of helmintic diseases as described herein. Such a mixture generally will contain unequal proportions of the milbemycin compounds, however, all of the compounds have substantial activity and the antiparasitic activity of the mixture can be accurately determined.

The compounds of this invention have a broad spectrum of activity against many internal parasites at low dosage levels and in many different animals. At levels of about 2.5 mg. per kg. of animal body weight, concentrated mixtures of milbemycin compounds may be administered to sheep infected with *Haemonchus contortus, Ostertagia circumcincta, Trichostrongylus axei, Trichostrongylus colubriformis, Cooperia spp.,* and *Oesophagostomum columbianum.* Similarly in cattle at dosages as low as 2.5 mg./kg. the milbemycin compounds may be used against *Ostertagia ostertagi, Trichostrongylus axei, Trichostrongylus colubriformis, Oesophagostomum radiatum* and *Dictyocaulus viviparus.* (In addition, horses infected with bots (*Gastrophilus intestinalis* and *Gastrophilus haemorrhoidalis*), large and small strongyles and Oxyuris may be treated with milbemycin.) In rodents, such as mice, infections of Syphacia, Nematospiroides and Aspiculuris may be treated by the oral administration of the milbemycin compounds or of the concentrates obtained from the extraction of the mycelia.

The anthelmintic activity of the milbemycin compounds may be determined by orally administering via the feed, a sample of milbemycin individual compound, a mixture of milbemycin compounds, a concentrated extract, and the like to mice which had been infected 3 days earlier with *Nematospiroides dubius.* At 11, 12 and 13 days after the initiation of the medication, the feces of the mice are examined for *N.dubius* eggs, and on the next day the mice are sacrificed and the number of worms present in the proximal portion of the small intestine are determined. An active compound is observed when there is a significant reduction of egg and worm counts when compared to infected, unmedicated controls.

What is claimed is:

1. A method for the treatment of helminthic infections which comprises administering to an animal infected with helminths an effective amount of one or more of the milbemycin compounds.

2. A method for the treatment of helminthic infections according to claim 1 wherein the milbemycin compound or compounds being administered is selected from the group consisting of milbemycin $\alpha_1, \alpha_2, \alpha_3, \alpha_4, \alpha_5, \alpha_6, \alpha_7, \alpha_8, \alpha_9, \alpha_{10}, \beta_1, \beta_2$ and $\beta_3$.

3. A method according to claim 2 wherein the milbemycin compound or compounds are selected from the group consisting of milbemycin $\alpha_1, \alpha_3, \alpha_5, \alpha_6$ and $\beta_1$.

4. The method of claim 3 wherein the milbemycin compound is milbemycin $\alpha_1$.

5. The method of claim 3 wherein the milbemycin compound is milbemycin $\alpha_3$.

6. The method of claim 3 wherein the milbemycin compound is milbemycin $\alpha_5$.

* * * * *